(12) United States Patent
Lopez-Marrero et al.

(10) Patent No.: US 11,726,071 B2
(45) Date of Patent: Aug. 15, 2023

(54) FINDING A CONTAMINANT SOURCE IN A VOLUME OF FLOWING FLUID

(71) Applicant: International Business Machines Corporation, Armonk, NY (US)

(72) Inventors: Vanessa Lopez-Marrero, Yorktown Heights, NY (US); Hendrik F. Hamann, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 1094 days.

(21) Appl. No.: 16/357,262

(22) Filed: Mar. 18, 2019

(65) Prior Publication Data

US 2020/0300828 A1 Sep. 24, 2020

(51) Int. Cl.
*G01N 33/00* (2006.01)
*G01M 3/04* (2006.01)

(52) U.S. Cl.
CPC .......... *G01N 33/0036* (2013.01); *G01M 3/04* (2013.01); *G01N 33/0073* (2013.01)

(58) Field of Classification Search
CPC .. G01M 3/04; G01N 33/0036; G01N 33/0073
See application file for complete search history.

(56) References Cited

U.S. PATENT DOCUMENTS

| 9,683,483 | B1 | 6/2017 | Bidner et al. | |
| 2012/0203516 | A1* | 8/2012 | Hamann | G06F 30/20 703/2 |
| 2014/0026641 | A1 | 1/2014 | Rella et al. | |
| 2016/0161456 | A1 | 6/2016 | Risk et al. | |
| 2018/0335544 | A1 | 11/2018 | Elmegreen | |

FOREIGN PATENT DOCUMENTS

WO  WO2018/075668 A1  4/2018

OTHER PUBLICATIONS

Wikipedia. Constructive solid geometry. https://en.wikipedia.org/wiki/Constructive_solid_geometry. Accessed Feb. 14, 2019. pp. 1-3.
Vanessa Lopez. Simulating Heat and Mass Transfer with Limited Amount of Sensor Data. Progress in Industrial Mathematics at ECMI 2016. Mar. 2018. pp. 1-7 (manuscript).

(Continued)

*Primary Examiner* — Matthew G Marini
*Assistant Examiner* — Leo T Hinze
(74) *Attorney, Agent, or Firm* — Daniel Morris; Otterstedt & Kammer PLLC

(57) ABSTRACT

A method includes: mapping a boundary of a volume of flowing fluid; partitioning the volume by a computational mesh; finding a contaminant location at a first sensor that is disposed within the volume; obtaining a measured velocity of the flowing fluid within the volume; generating a reversed velocity vector field within the mesh, in response to the measured velocity; time stepping the contaminant location from the first sensor along the reversed velocity vector field until the contaminant location intersects the boundary of the volume; and finding a contaminant source at the intersection of the time stepped contaminant location with the boundary of the volume.

14 Claims, 5 Drawing Sheets

(56) References Cited

OTHER PUBLICATIONS

E. P. Olaguer. "Adjoint model enhanced plume reconstruction from tomographic remote sensing measurements". Atmospheric Environment, 45(38). Dec. 2011. pp. 6980-6986.
Sergiy Zhuk et al. "On source-term parameter estimation for linear advection-diffusion equations with uncertain coefficients". SIAM J. Sci. Comput. vol. 38, No. 4. Aug. 2016. pp. 1-19.
The OpenFOAM Foundation. "OpenFOAM v6 User Guide". https://cfd.direc/openfoam/user-guide. Table of Contents. pp. 1-7 downloaded Mar. 18, 2019 bears date Mar. 2, 2017.
Poungkrajorn , Assuring asset integrity through improving the accuracy of leakage source identification of a permanently installed subsea leak detection system using artificial neural networks, Master's thesis, University of Stavanger, Norway, 2015.
Brereton et al., Fugitive emission source characterization using a gradient-based optimization scheme and scalar transport adjoint, Atmospheric Environment 181, 2018, pp. 106-116.
Van Kessel et al., Methane leak detection and localization using wireless sensor networks for remote oil and gas operations, In 2018 IEEE Sensors, pp. 1-4. IEEE, 2018.
Klein et al., Wireless sensor networks for fugitive methane emissions monitoring in oil and gas industry, In 2018 IEEE International Congress on Internet of Things (ICIOT), pp. 41-48, IEEE, 2018.
Bernhard Hustedt, European Patent Office as ISA, Patent Cooperation Treaty Written Opinion, PCT/EP2020/050242, dated Apr. 9, 2020, 9 pages.
Bernhard Hustedt, European Patent Office as ISA, Patent Cooperation Treaty International Search Report, PCT/EP2020/050242, dated Apr. 9, 2020, 7 pages.

\* cited by examiner

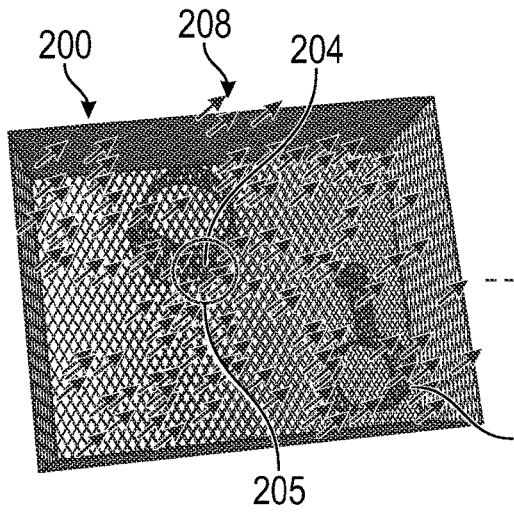
FIG. 3
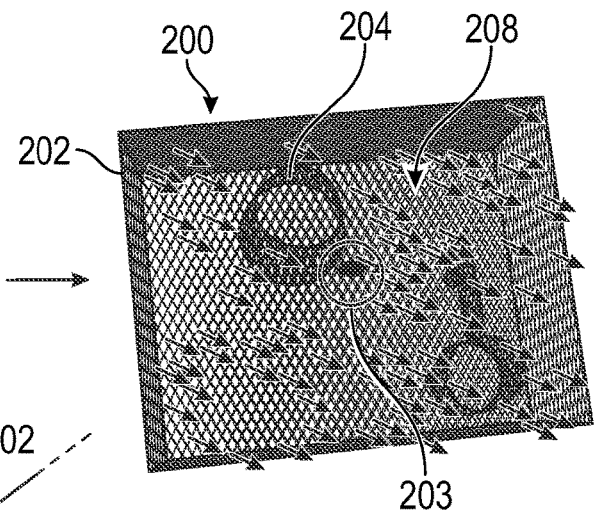
FIG. 4
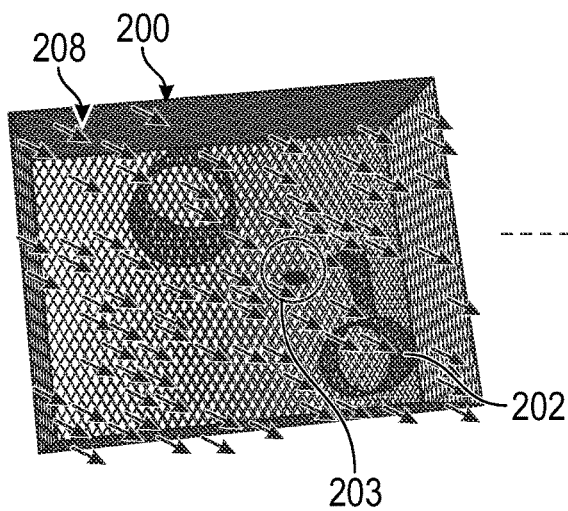
FIG. 5
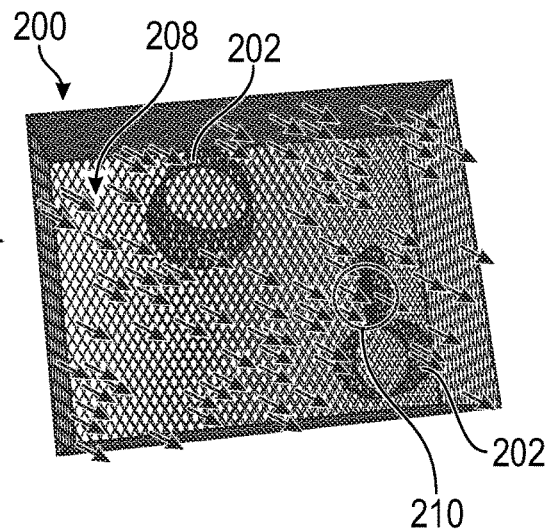
FIG. 6
$t_0 = \tau_0 = \tau;\ t_n = t_{n-1} + \delta, \tau_n = \tau_{n-1} - \delta;$
$\wedge(x, t_n) = -v(x, \tau_n)$
$\partial a/\partial t + \nabla \bullet (a\wedge) = \nabla \bullet (k\nabla a)\ in\ \Omega$      (1)
IC: $a(x, \tau_0) = \gamma > 0\ if\ x \in \Sigma;\ 0\ otherwise$      (2)
BCs: $n \bullet \nabla a(x, t) = 0\ on\ \Gamma 1$      (3)
$a(x, t) = 0\ if\ t = \tau_0$ or
$a(x_\varepsilon, t-\delta)\ otherwise,\ on\ \Gamma 2$      (4)
FIG. 7

FINDING A CONTAMINANT SOURCE IN A VOLUME OF FLOWING FLUID

STATEMENT REGARDING FEDERALLY SPONSORED RESEARCH OR DEVELOPMENT

This invention was made with Government support under Contract No.: DE-AR0000540 awarded by Department of Energy. The Government has certain rights in this invention.

BACKGROUND

The present invention relates to chemical sensing equipment and more specifically, to detection of contaminants in fluids.

Methane leaks in a natural gas field produce a hazard not only for the environment but also for safety. Generally, methane is an environmentally friendly fuel because when it is burned, it releases less carbon dioxide per unit energy than is produced by burning other hydrocarbons. Thus, burning methane rather than other fuels is one way to mitigate greenhouse gas emissions. However, methane itself is more potent than carbon dioxide as a greenhouse gas. Thus, releases of methane from a gas field, i.e. by leaks, can detract from the overall impact of methane for reducing global warming. In fact, excessive leakage of methane eliminates its emission-reducing benefits as a fuel. Additionally, methane leaks are a safety risk due to flammability or explosion. Real-time monitoring of methane concentration in air, within gas fields, helps mitigate the environmental and safety risks.

SUMMARY

Principles of the invention provide techniques for finding a contaminant source in a volume of flowing fluid. In one aspect, an exemplary method includes mapping a boundary of a volume of flowing fluid; partitioning the volume by a computational mesh; finding a contaminant location at a first sensor that is disposed within the volume; obtaining a measured velocity of the flowing fluid within the volume; generating a reversed velocity vector field within the mesh, in response to the measured velocity; time stepping the contaminant location from the first sensor along the reversed velocity vector field until the contaminant location intersects the boundary of the volume; and finding a contaminant source at the intersection of the time stepped contaminant location with the boundary of the volume.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory that embodies computer executable instructions, and at least one processor that is coupled to the memory and operative by the instructions to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

In view of the foregoing, techniques of the present invention can provide substantial beneficial technical effects. For example, one or more embodiments provide Rapid and precise localization of contaminant sources in a volume of flowing fluid.

These and other features and advantages of the present invention will become apparent from the following detailed description of illustrative embodiments thereof, which is to be read in connection with the accompanying drawings.

BRIEF DESCRIPTION OF THE DRAWINGS

FIGS. 3-6 depict schematically time steps of the method shown in FIG. 1, from detection of a contaminant at a sensor within a meshed volume of flowing fluid to localization of a contaminant source within the meshed volume, according to an exemplary embodiment;

FIG. 7 presents equations for a boundary value problem that is solved to localize the contaminant source, according to an exemplary embodiment;

DETAILED DESCRIPTION

One exemplary embodiment of the invention relates to detection and localization of methane leaks within a bounded volume of air flowing through a natural gas field. By localizing a leak to a particular piece of piping, or to a boundary of the field, a gas field operator can determine whether it is possible to mitigate the leak, and how to do so. Other embodiments may relate to detection and localization of contaminant sources in other bounded volumes of flowing fluid, e.g., in a body of water.

Figure 1:
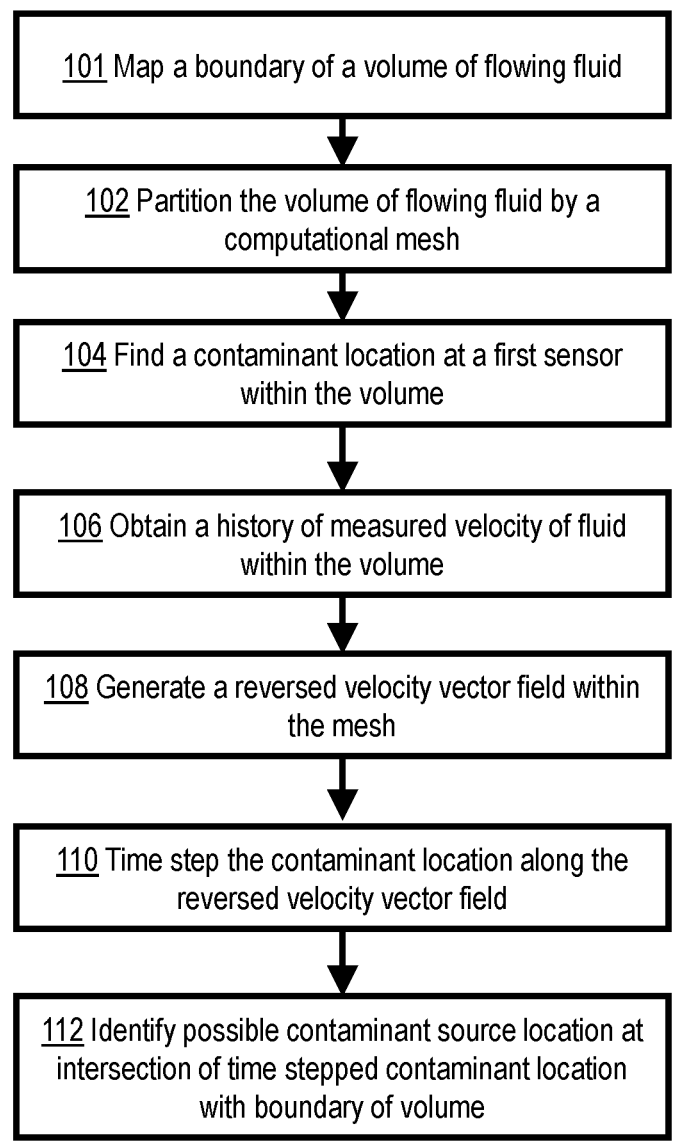
FIG. 1 depicts in a flowchart a method for finding a contaminant source in a volume of flowing fluid, according to an exemplary embodiment.
Figure 2:
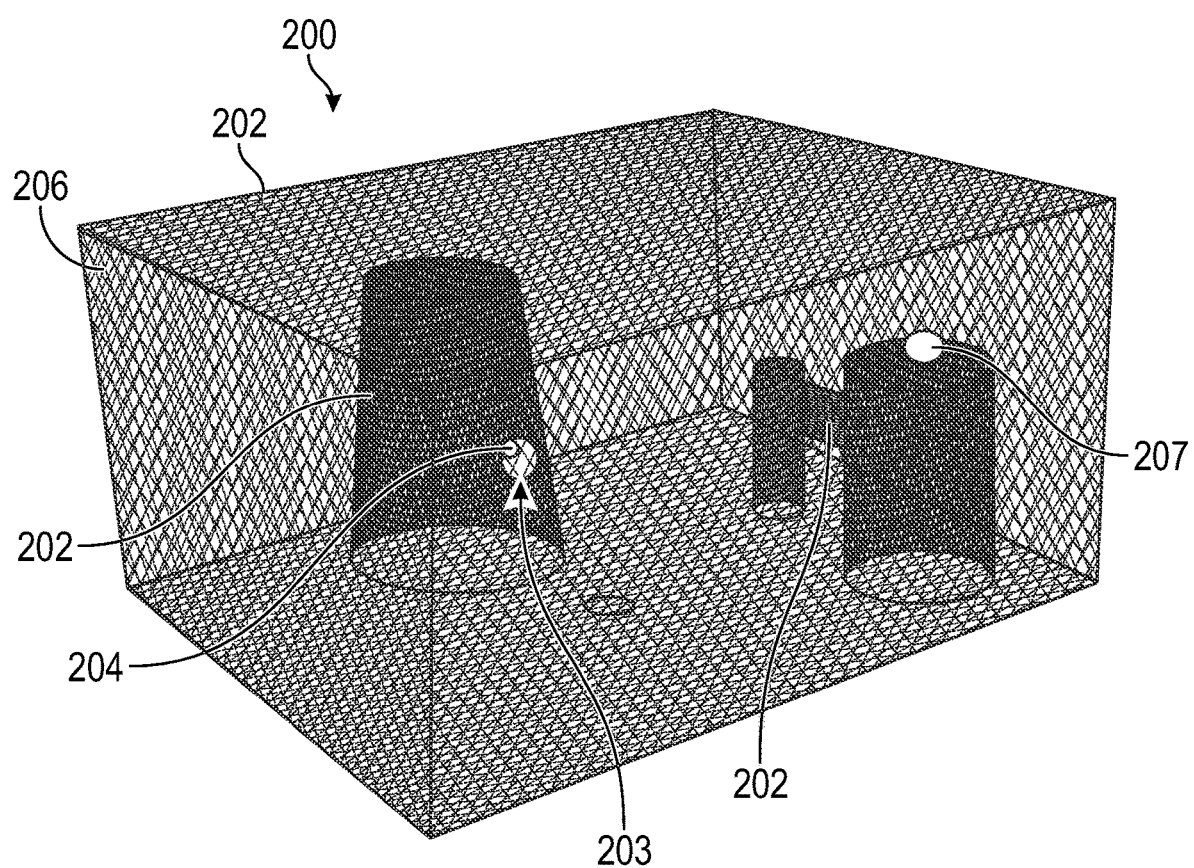
FIG. 2 depicts a volume of flowing fluid, partitioned by a computational mesh according to an exemplary embodiment.

According to the exemplary embodiment, and with reference to FIGS. 1 and 2, a method 100 is implemented for a volume 200 of flowing fluid (e.g., air) by first performing a step 101 of mapping a boundary 202 of the volume 200. In one or more embodiments, the boundary 202 can be defined using constructive solid geometry (CSG). Constructive solid geometry is explained, for example, in an eponymous Wikipedia article, hereby incorporated by reference in its entirety. At 102, the method 100 continues with partitioning the volume 200 by a mesh 206 for computational purposes. The method 100 continues at 104 by finding a contaminant location 203 (e.g., a set of nodes or elements within a spherical region in the mesh 206) at a first sensor 204 (e.g., a methane sensor) that is disposed within the volume 200 of flowing fluid. At 106, obtain a history of measured velocity of the flowing fluid, going back from the time that the contaminant location is found, e.g., by a velocity sensor 207 that is disposed within the volume 200. Referring now also to FIGS. 3-6, at 108, generate a reversed velocity vector field 208 (shown in FIGS. 3-6, omitted from FIG. 2) within the mesh. The reversed velocity vector field mirrors the history of measured velocities in time, i.e. the reversed velocity vector field goes forward in time from when the contaminant location was found whereas the history of measured velocities goes backward in time. It should be noted that a velocity sensor 207 can typically be placed on the ground or other solid boundary, since the outer boundaries of the gas field are (likely) open, i.e., not solid.

For example, in one or more embodiments generating the reversed velocity vector field 208 includes setting the velocity vector field at time $t_n = t_0 + \delta$ uniformly equal to a reversed value of the measured velocity at time $\tau_n = \tau_0 - \delta$.

Alternatively, in one or more embodiments obtaining the reversed velocity vector field 208 includes setting the measured velocity as a boundary condition of computational fluid dynamics (CFD) equations that describe the flowing fluid within the boundary of the volume, solving the computational fluid dynamics equations to estimate a "true" velocity vector field, and then reversing the "true" velocity vector field. In one or more embodiments, the boundary 202 of the volume includes surfaces of components within the volume (in a non-limiting example, equipment such as pipes, valves, and tanks in a natural gas field), and the surfaces of the components also set boundary conditions for the CFD equations. Software such as the OpenFOAM open source software can be used for solving the CFD equations. The OpenFOAM open source software is described, for example, at the openfoam dot org web site, hereby incorporated by reference in its entirety.

Alternatively, in one or more embodiments obtaining the reversed velocity vector field 208 includes making a direct measurement of the velocity vector field, e.g., by laser scattering, then reversing the directly measured velocity vector field. In such embodiments the laser is a part of the velocity sensor 207, which optionally may be located outside the volume 200.

At 110, the method 100 continues by time stepping the contaminant, represented by a scalar function a(x,t), starting at the contaminant location 203 (as shown in FIGS. 3-5) from the first sensor 204 and transporting the contaminant along the reversed velocity vector field 208 until the contaminant location intersects a portion of the boundary 202 of the volume 200 at a source location 210 (as seen in FIG. 6). The time stepping is accomplished (as further discussed below with reference to FIG. 8) by solving a boundary value problem for scalar transport, via a system of equations as shown in FIG. 7, which presumes either a uniform velocity vector field, a solution to the CFD equations for the velocity vector field, or a directly measured velocity vector field. One or more embodiments solve the boundary value problem in the normal "forward" time direction, using the reversed velocity vector field 208, which effectively "mirrors" the results back in time to the original source of the contaminant.

In FIG. 7, $\tau_0 = t_0 = \tau$ is a time at which the sensor 204 detects methane above a given threshold. $t_n$ is an increment of "normal" forward-stepping time; $\tau_n$ is an increment of "reverse" time. $\tau_n$ mirrors $t_n$ around $t_0 = \tau_0$. The set of nodes or elements within the mesh 206 (described as the solution domain $\Omega$ in the equations of FIG. 7) have spatial coordinates that are denoted by x. $v(x,\tau_n)$ is the actual velocity vector field at time $\tau_n$ preceding $\tau_0$. $\Lambda(x,t_n)$ is the reversed velocity vector field 208 at time $t_n$ following $t_0$. $a(x,t_n)$ is a scalar field of contaminant concentrations in the fluid at time $t_n$. $\Sigma$ denotes points or cells in the mesh 206 that make up a ball of radius r>0 (corresponding to the contaminant location 203) that is centered at the location of the sensor 204.

An initial condition (IC) a(x,0) (i.e., equation (2)) is established for the boundary value problem (BVP) for scalar transport. For $x \in \Sigma$, a(x,0) is non-zero (i.e. the measured concentration of contaminant); for other x, a(x,0) is set to zero. A boundary condition (BCs) of zero gradient for a(x,t) (i.e., equation (3)) is established for $x \in \Gamma_1$ (where $\Gamma_1$ is the set of nodes or elements at a portion of the boundary 202 that is the surface of a solid object such as the ground, a pipe, valve, or tank within the volume 200). A boundary condition of fixed value for a(x,t) (i.e., equation (4)) is established for $x \in \Gamma_2$ (where $\Gamma_2$ is the set of nodes or elements at a portion of the boundary 202 that is an external boundary of the volume 200 and $x_\epsilon$ represents the set of interior mesh points that are closest to each x that is a member of $\Gamma_2$). The variable II denotes a time step counter in a computational loop that is implemented according to FIG. 8 as discussed below. The parameter k represents a diffusion coefficient for contaminant in fluid. The parameter $\gamma$ is a concentration of contaminant at the initial condition of the boundary value problem.

At 110, the BVP shown in FIG. 7 is repeatedly solved at increments $\delta$ of time $t_n = t + \delta$, until a pre-set amount of time has expired or until no more information is available for the fluid's reversed velocity vector field 208, keeping a record of the spatial locations $x \in \Gamma_1$ or $x \in \Gamma_2$ at which a(x,t) is non-zero. (In other words, keeping a record of those spatial locations on the boundary of the volume where the nonzero value of the IC (2) from FIG. 7 is transported to by the reversed fluid velocity field.)

Then at 112, the method 100 concludes by identifying a list of possible contaminant source locations (e.g. location 210) at the intersection of the time stepped contaminant location 203 with the boundary 202 of the volume 200—i.e., at the location 210 where a(x,t)>0 for $x \in \Gamma_1$ or $x \in \Gamma_2$. In FIGS. 3-6, an example is shown in which the location 210 is found at an internal boundary, i.e. piping structure within the volume 200. However, aspects of the invention are equally applicable when the location 210 is found at an external boundary of the volume 200.

Physical locations corresponding to sections of the boundary 202 that have been identified as possible contaminant sources 210, as well as the sub volume $\Sigma$ around the sensor that has been identified as the "original" contaminant location 203, then can be used as initial guesses to solve a suitable inverse problem or can be inspected (and, if necessary, repaired) as deemed appropriate.

One exemplary inverse problem is to determine characteristics of a gas plume, e.g., emission source strength; emission error variance; horizontal diffusion coefficient; horizontal diffusion coefficient error variance; maximum background concentration error covariance; and remote sensing observational error variance. Such an inverse problem is described, for example, in a paper titled "Adjoint model enhanced plume reconstruction from tomographic remote sensing measurements" by E. P. Olaguer in Atmospheric Environment, 45 (2011), hereby incorporated by reference in its entirety. These variables are properties of a gas plume, which may give useful information, for example, to be able to quantify a leak, or simulate the expansion of the gas plume as time evolves. Thus, in order to be able to solve the problem to determine such characteristics, knowing the location of the leak (where the plume originates) is helpful.

Another exemplary inverse problem is to solve for the precise spatial coordinates of where a contaminant has been introduced to a flowing fluid. Such an inverse problem is described, for example, in a paper titled "On source-term parameter estimation for linear advection-diffusion equations with uncertain coefficients" by S. Zhuk et al. in SIAM J. Sci. Comput. Vol. 38, No. 4 (2016), hereby incorporated by reference in its entirety. To solve such an inverse problem numerically, a starting guess is needed and a choice of the starting guess can sometimes be crucial to be able to find a solution efficiently or even at all. The methods of the present invention can provide a useful starting guess for numerical solution of such an inverse problem.

Figure 8:
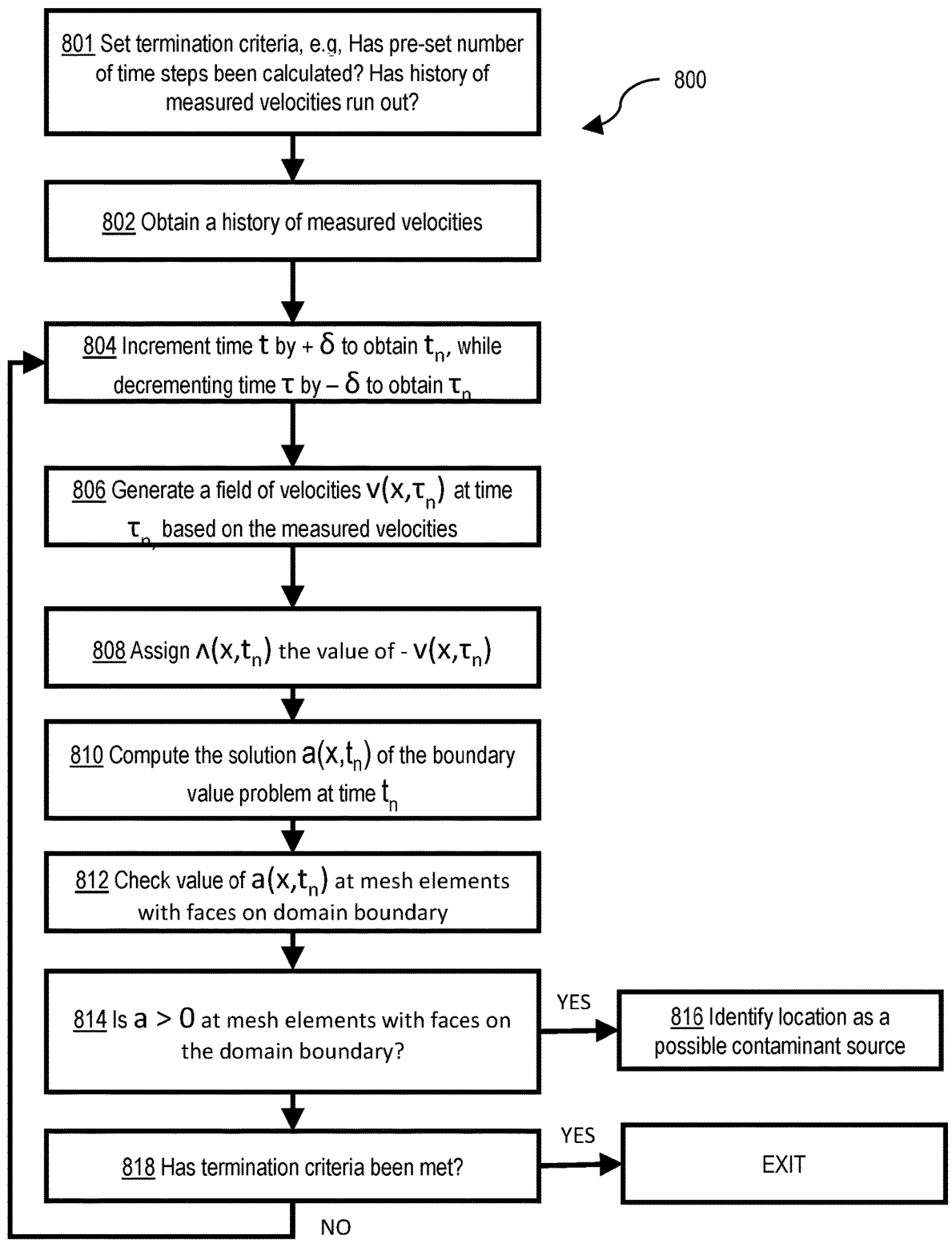
FIG. 8 depicts in a flowchart a computational loop portion of the method of FIG. 1.

FIG. 8 depicts in more detail a computational loop algorithm 800 that is implemented at step 110 of FIG. 1. At 801, set termination criteria, e.g., whether a pre-set number of time steps have been calculated, whether an estimated contaminant location has reached a boundary of the volume, whether a history of measured velocities has run out, or the like. At 802, obtain a history of measured velocities. At 804, increment time t by +δ to obtain $t_n$, while decrementing time τ by −δ to obtain $\tau_n$. At 806, generate a historical field of velocities $v(x,\tau_n)$, based on the measured velocity(ies) for time $\tau_n$. At 808, assign $\Lambda(x,t_n)$ the value of $-v(x,\tau_n)$. At 810, solve the boundary value problem of FIG. 7 for $a(x,t_n)$. At 812, check the value of $a(x, t_n)$ at mesh elements with faces on the boundary δΩ of the domain Ω (analogously, at nodes on the boundary). At 814, if a>0 at mesh elements with a face on the boundary, then at 816 identify the location as a possible source of contaminant. At 818, evaluate whether the termination criteria 801 has been met. If YES, terminate the computational loop; if NO, return to 804. In some cases a contaminant source will be identified at a boundary of the volume of flowing fluid, while in other cases (e.g., time or velocity history expires) a possible contaminant source will be identified within the volume of flowing fluid. In the latter case, the possible contaminant source can be used as a starting point for solving an inverse problem as discussed above.

In one or more embodiments, the time stepping is accomplished by reversing a velocity vector field and stepping forward in time.

One or more embodiments of the method 100 also include expanding a radius of the contaminant location 203 during the time stepping.

In one or more embodiments, the methodology described could be part of a more general data management system which, in addition to storing measured data, could also trigger certain processes automatically. For instance, the data management system could be programmed so that when it detects a methane sensor reading above a given threshold, the methods of the present invention automatically are triggered (i.e., without human intervention). Efficiency of computation could be enhanced in at least the following ways:

1. Since the geometry of the gas field may be expected to not be constantly changing, one could compute and store the mesh beforehand and have some flag indicating (the date) when anything relevant in the geometry changes. When the method gets triggered, the mesh would only need to be recomputed if the "mesh flag" indicates it. That would save some computational time.
2. The data management system could store up-to-date values for the physical locations of the sensors, as part of pre-mapping the mesh.
3. The data management system could be programmed with various options and best possible choice for obtaining or generating the fluid velocity vector field and its history. Storing the history of fluid velocity vector field in the data management system could save computational time.

In one or more embodiments, completion of the methodology as described above can trigger a remedial action to mitigate the localized source of a contaminant. For example, a computer server system (e.g., a computer server 10 such as shown and described with reference to FIG. 9, below), which implements the method 100, alerts maintenance personnel first to temporarily stop flow of the contaminant (e.g., halt flow of methane through gas field piping; halt discharge of steam from a cooling tower) and then to permanently repair the source of the contaminant (e.g., patch gas piping or boiler tubes). Computer 10 could also automatically activate an isolation valve to stop the leak until a repair can be effectuates; e.g., by a signal over network adapter 20 or interface 22 or the like (discussed below).

Given the discussion thus far, and with reference to the accompanying drawings, it will be appreciated that, in general terms, an exemplary method 100, according to an aspect of the invention, includes 101 mapping a boundary 202 of a volume 200 of flowing fluid; 102 partitioning the volume by a computational mesh 206; 104 finding a contaminant location 203 at a first sensor 204 that is disposed within the volume; 106 obtaining a measured velocity of the flowing fluid within the volume at a past time; 108 generating a reversed velocity vector field 208 within the mesh, in response to the measured velocity; 110 time stepping the contaminant location from the first sensor into future time along the reversed velocity vector field, while time stepping the reversed velocity vector field into past time, until the contaminant location intersects the boundary of the volume; and 112 finding a contaminant source 210 at the intersection of the time stepped contaminant location with the boundary of the volume.

In one or more embodiments, generating the reversed velocity vector field includes setting a velocity vector field uniformly equal to the measured velocity and then reversing the velocity vector field.

In one or more embodiments, generating the reversed velocity vector field includes setting the measured velocity as a boundary condition of computational fluid dynamics equations that describe the flowing fluid within the boundary of the volume, solving the computational fluid dynamics equations to estimate a velocity vector field, and reversing the velocity vector field to generate the reversed velocity vector field.

In one or more embodiments, the boundary of the volume includes surfaces of components within the volume, and the surfaces of the components set boundary conditions of the computational fluid dynamics equations.

In one or more embodiments, the method also includes expanding a radius of the contaminant location during the time stepping.

In one or more embodiments, the boundary of the volume includes surfaces of components within the volume.

In one or more embodiments, the method also includes solving an inverse problem using the contaminant source as an initial guess.

In one or more embodiments, efficiency of the computation is improved by pre-computing and storing the computational mesh and updating the computational mesh when the boundary of the volume is updated.

In one or more embodiments, the method also includes implementing an action to mitigate the contaminant source, wherein the action includes at least one of securing flow to the contaminant source or repairing a leak at the contaminant source.

Figure 9:
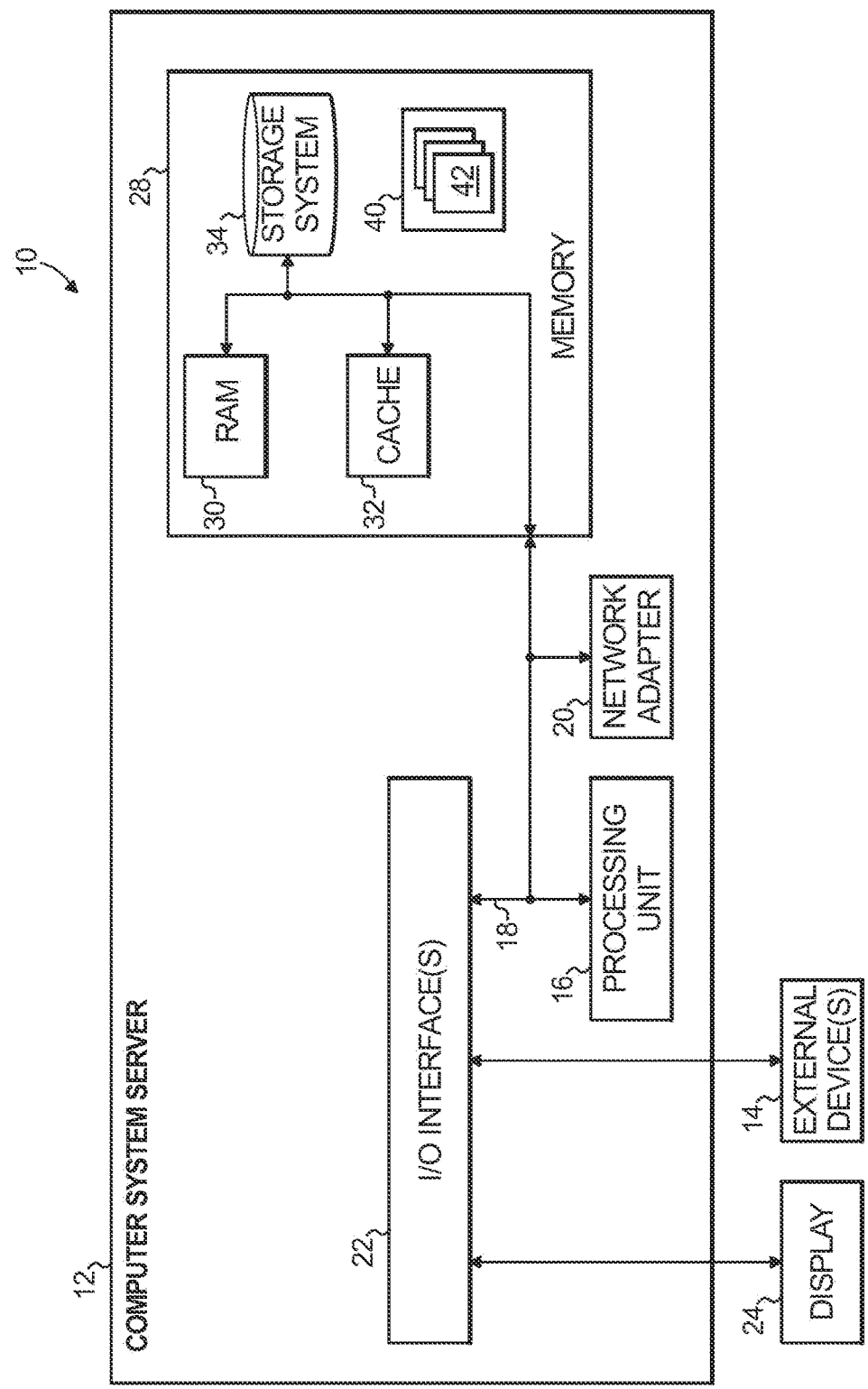
FIG. 9 depicts an exemplary computer server system for implementing the method of FIG. 1.

One or more embodiments of the invention, or elements thereof, can be implemented in the form of an apparatus including a memory and at least one processor that is coupled to the memory and operative to perform exemplary method steps, or in the form of a non-transitory computer readable medium embodying computer executable instructions which when executed by a computer cause the computer to perform exemplary method steps. FIG. 9 depicts a computer system 10 that may be useful in implementing one or more aspects and/or elements of the invention. Referring now to FIG. 9, system 10 is in the exemplary form of a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed computing environments where tasks are performed by remote processing devices that are linked through a communications network. In a distributed computing environment, program modules may be located in both local and remote computer system storage media including memory storage devices. Other embodiments could be local and not distributed.

As shown in FIG. 9, computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 9, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 9) running a server program. It will be understood that such a physical server may or may not include a display and keyboard.

One or more embodiments can be at least partially implemented in the context of a virtual machine environment, although this is exemplary and non-limiting.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for operating a natural gas field that comprises pipes, valves, and tanks, the method comprising:
    mapping a boundary of a volume of flowing fluid above the natural gas field;
    positioning sensors in the volume of flowing fluid;
    partitioning the volume by a computational mesh, wherein efficiency of computation is improved by pre-computing and storing the computational mesh and updating the computational mesh when the boundary of the volume is updated;
    finding a contaminant location by detecting the contaminant at a first sensor that is disposed within the volume;
    obtaining a measured velocity of the flowing fluid within the volume at a past time, wherein efficiency of the computation is improved by retrieving a stored history of the measured velocity of the flowing fluid;
    generating a reversed velocity vector field within the mesh, in response to the measured velocity;
    time stepping the contaminant location from the first sensor into future time along the reversed velocity vector field, while time stepping the reversed velocity vector field into past time, until the contaminant location intersects the boundary of the volume;
    finding a contaminant source at the intersection of the time stepped contaminant location with the boundary of the volume;
    solving an inverse problem using the contaminant source as an initial guess; and
    mitigating the contaminant source by at least one of securing flow through one or more of the pipes or patching one or more of the pipes.

2. The method of claim 1 wherein generating the reversed velocity vector field includes setting a velocity vector field uniformly equal to the measured velocity and then reversing the velocity vector field.

3. The method of claim 1 wherein generating the reversed velocity vector field includes setting the measured velocity as a boundary condition of computational fluid dynamics equations that describe the flowing fluid within the boundary of the volume, solving the computational fluid dynamics equations to estimate a velocity vector field, and reversing the velocity vector field to generate the reversed velocity vector field.

4. The method of claim 3 wherein the boundary of the volume includes surfaces of components within the volume, and the surfaces of the components set boundary conditions of the computational fluid dynamics equations.

5. The method of claim 3 wherein efficiency of the computation is improved by pre-computing and storing the reversed velocity vector field.

6. The method of claim 1 further comprising expanding a radius of the contaminant location during the time stepping.

7. The method of claim 1 wherein the boundary of the volume includes surfaces of components within the volume.

8. A non-transitory computer readable medium embodying computer executable instructions which when executed by a computer cause the computer to facilitate a method for operating a natural gas field that comprises pipes, valves, and tanks, the method comprising:
- mapping a boundary of a volume of flowing fluid above the natural gas field;
- positioning sensors in the volume of flowing fluid;
- partitioning the volume by a computational mesh, wherein efficiency of computation is improved by pre-computing and storing the computational mesh and updating the computational mesh when the boundary of the volume is updated;
- finding a contaminant location by detecting the contaminant at a first sensor that is disposed within the volume;
- obtaining a measured velocity of the flowing fluid within the volume at a past time, wherein efficiency of the computation is improved by retrieving a stored history of the measured velocity of the flowing fluid;
- generating a reversed velocity vector field within the mesh, in response to the measured velocity;
- time stepping the contaminant location from the first sensor along the reversed velocity vector field until the contaminant location intersects the boundary of the volume;
- finding a contaminant source at the intersection of the time stepped contaminant location with the boundary of the volume;
- solving an inverse problem using the contaminant source as an initial guess; and
- mitigating the contaminant source by at least one of securing flow through one or more of the pipes or patching one or more of the pipes.

9. The medium of claim 8 wherein generating the reversed velocity vector field includes setting a velocity vector field uniformly equal to the measured velocity and then reversing the velocity vector field.

10. The medium of claim 8 wherein generating the reversed velocity vector field includes setting the measured velocity as a boundary condition of computational fluid dynamics equations that describe the flowing fluid within the boundaries of the volume, solving the computational fluid dynamics equations to estimate a velocity vector field, and reversing the velocity vector field to generate the reversed velocity vector field.

11. The medium of claim 10 wherein the boundaries of the volume include surfaces of components within the volume, and the surfaces of the components set boundary conditions of the computational fluid dynamics equations.

12. The medium of claim 8, the method further comprising expanding a radius of the contaminant location during the time stepping.

13. The medium of claim 8 wherein the boundaries of the volume include surfaces of components within the volume.

14. The medium of claim 8, the method further comprising solving an inverse problem using the contaminant source as an initial guess.

* * * * *